United States Patent [19]

Mark et al.

[11] 4,291,177

[45] Sep. 22, 1981

[54] PROCESS FOR OBTAINING HALOGENATED DIPHENOLS

[75] Inventors: Victor Mark, Evansville, Ind.; Charles A. Wilson, II, Greenville, S.C.

[73] Assignee: General Electric Company, Mt. Vernon, Ind.

[21] Appl. No.: 100,864

[22] Filed: Dec. 6, 1979

Related U.S. Application Data

[63] Continuation of Ser. No. 882,191, Feb. 28, 1978.

[51] Int. Cl.³ .................... C07C 39/16; C07C 43/23; C07C 39/00; C07C 147/10; C07C 147/14
[52] U.S. Cl. ........................... 568/726; 568/48; 568/725; 568/33; 568/37; 568/56; 568/729; 568/65; 568/587; 568/588; 568/637; 568/638

[58] Field of Search .................... 568/726, 27, 55, 56, 568/58, 587, 588, 28, 638, 637, 725, 48, 65, 33, 37, 729

[56] References Cited

U.S. PATENT DOCUMENTS 4,075,119  2/1978  Schmidt et al. ..................... 568/726

FOREIGN PATENT DOCUMENTS 2520316  11/1976  Fed. Rep. of Germany ...... 568/726

*Primary Examiner*—Werren B. Lone
*Attorney, Agent, or Firm*—Martin B. Barancik; William F. Mufatti

[57] ABSTRACT

Highly pure dihalodiphenols or predetermined, statistical mixtures of unreacted, monohalo- and dihalodiphenols are obtained reacting the diphenol, which is suspended or dissolved in a suitable solvent, with a halogen while concurrently purging the reaction with a gas that is inert to the reaction.

13 Claims, No Drawings

PROCESS FOR OBTAINING HALOGENATED DIPHENOLS

This is a continuation of application Ser. No. 882,191 filed Feb. 28, 1978.

This invention relates to an improved process for obtaining halogenated diphenols. More particularly, this invention relates to an improved process that permits the reaction to be closely controlled enabling pure dihalodiphenols or predetermined, statistical mixtures of halogenated diphenols to be obtained.

BACKGROUND OF THE INVENTION

It is known to prepare halogenated diphenols which can be used as anti-mildew agents, fungicides, fire retardant agents in various polyesters, monomers for the preparation of aromatic polycarbonates, and the like.

The preparation of halophenols, including halodiphenols, halotriphenols, halotetraphenols, etc., is often desired to improve the properties of the parent phenol. For instance, the halogenated phenols often possess enhanced, desirable biological properties, compared with nonhalogenated phenols and have been manufactured on a large scale. For example, pentachlorophenol is potent wood preservative, pentabromophenol is a component of flame retardant formulations, 2,2'-methylenebis(3,4,6-trichlorophenol) is a potent and useful bactericide, and 4,4'-isopropylidenebis(2-chlorophenol) has been used as an anti-mildew agent. Often, derivatives of halophenols are also useful such as polymers derived from 4,4'-isopropylidenebis(2,6-dibromophenol) and the corresponding bis(dichlorophenol) which, in the form of polyesters and polycarbonates, possess outstanding flame-retardant characteristics as is known in the prior art.

The preparation of halophenols is customerily carried out by direct halogenation with elemental chlorine and/or bromine. In the case of simple or stable molecules, this appears to be the simplest process. However, when it is applied to more complicated and sensitive structures, it often yields by-products that can seriously interfere with the intended end-use of the halophenols. For instance, U.S. Pat. No. 3,062,781 discloses halogenated diphenols which are obtained by a direct halogenation procedure which require further treatment with sodium hydroxide and triethylamine at 80° C. before they can be converted to polycarbonates of acceptable stability. Such a treatment is necessary in order to remove aliphatically bound halogens formed in the halogenation process. It has been found that these aliphatically bound halogen compounds, which are generally recognizable by their red color, are formed by the cleavage reaction exerted by the hydrogen halide coproduct on the diphenol. For example, when 4,4'-isopropylidenediphenol (BPA) is employed, the chlorination reaction produces an equimolar amount of hydrogen chloride coproduct as shown below:

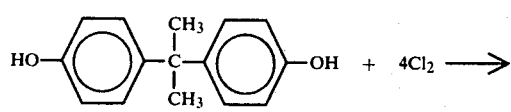

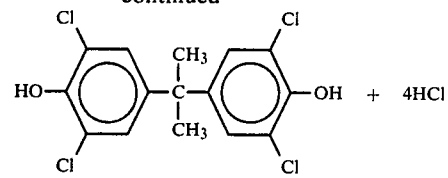

The HCl coproduct produced in (I) above effects a cleavage reaction on BPA or its chlorinated derivatives as shown below:

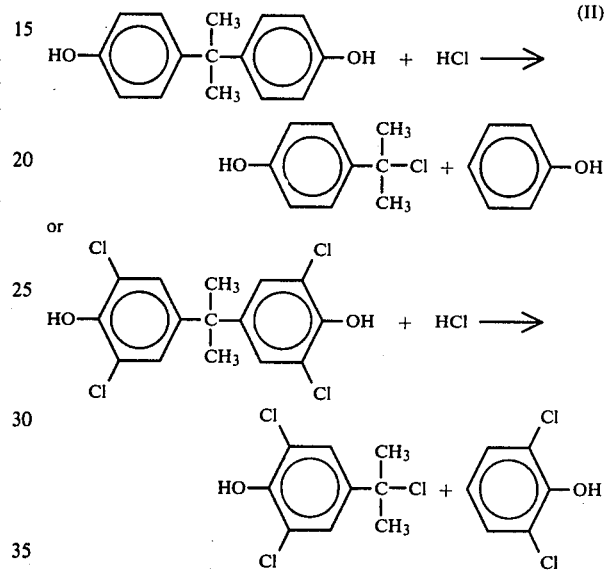

Thus, the chloroisopropylphenols cause the discoloration and the chlorinated phenols also have a disagreeable odor. The formation of by-products is even more pronounced in bromination processes.

German Pat. No. P25 317.2 discloses two methods for brominating and/or chlorinating bisphenols; namely, a gas-solid phase method and a suspension method. From these methods, there are obtained a mixture of unreacted bisphenol and statistical mixtures of halogenated bisphenols which are used to prepare polycarbonates having improved fire retardant properties.

In the suspension method disclosed in this German patent, the bisphenol is suspended in a halogen-containing hydrocarbon to produce a halogenated bisphenol. The halogen-containing hydrocarbons disclosed are carbon tetrachloride and tetrachloroethane, carbon tetrachloride being preferred.

While the suspension method disclosed in the above-identified German patent is of interest, it is not entirely satisfactory. For example, since bisphenols are not very soluble in either carbon tetrachloride or tetrachloroethane, excess halogen, i.e., either bromine and/or chlorine, must be used to assure halogenation of the bisphenols. As a result, a significant amount of halogen is lost in the system during the reaction and the rate of halogenation cannot be closely controlled. Thus, this method produces an excess of unreacted bisphenols and, primarily, tri- and tetrahalogenated bisphenols which, when further processed to produce a polycarbonate, do not impart good impact properties to the polycarbonate. Furthermore, the halogenated bisphenols must be isolated from the solvent system before they can be subjected to polymerization to obtain polycarbonates.

Co-pending application Ser. No. 882,192, filed Feb. 28, 1978, and assigned to the same assignee as this case discloses a continuous process for producing high molecular weight polycarbonates including halogenating diphenols wherein the diphenol is dissolved or suspended in a solvent system comprising methylene chloride and water and metering a halogen gas into the solvent system. In that process, water is used to react with the hydrogen halide produced and thereby minimize the formation of undesirable by-products.

Co-pending application Ser. No. 882,242, filed Feb. 28, 1978, also assigned to the same assignee as this case, discloses a process for halogenating diphenols wherein the diphenol is dissolved or suspended in methylene chloride and then contacted with sulfuryl chloride which reacts with the halogen halide produced in a "self-sweeping" reaction thereby minimizing the formation of undesirable by-products. In this process, bromine can also be incorporated concurrently with the sulfuryl chloride.

SUMMARY OF THE INVENTION

It has now been found that halogenated diphenols obtainable in high purity can be prepared by suspending or dissolving the diphenol in a suitable solvent such as methylene chloride and thereafter reacting the diphenol with a halogen or mixture of halogens to obtain a halogenated diphenol either in high purity or having a predetermined degree of halogen content and a neglible amount of deleterious by-products. Since this process results in minimizing impurities as well as minimizing the formation of undesirable by-products, the highly pure halogenated diphenol obtained need not be treated further before being used. These halogenated diphenols can be used as anti-mildew agents, fungicides, fire retardant agents in various polyesters, monomers for the preparation of aromatic polycarbonates, and the like.

The process of this invention can be made continuous and is based on using quantitative amounts of reactants thereby enabling the extent of halogenation to be closely controlled. As a result, all of the halogen employed is reacted with the diphenol so that there is realized not only a savings in material and labor cost, but a savings in time as well as increased product yield. Accordingly, the process of the invention can be adapted for use with other processes to continuously produce such materials as fire retardant polyesters, aromatic polycarbonates, and the like.

The solvent system of the present invention can be either chlorobenzene or methylene chloride, methylene chloride being preferred, and can be present in amounts sufficient to result in a clear solution when the halogenation reaction is complete.

In order to prevent or minimize the deleterious effect on the hydrogen halide produced during the reaction which can result in the formation of undesirable by-products, the reaction is concurrently purged with an inert gas such as $CO_2$, $N_2$, $SO_2$, noble gas, and the like, which is inert to the reaction. The inert gas serves to sweep the hydrogen halide out of the reaction vessel and thereby prevent its attack upon the reacted diphenol. While it is possible to use any of the halides, chlorine and bromine are preferred.

The following equation exemplifies the reaction of the process of the invention using, as the diphenol, bisphenol-A; i.e., 4,4'-isopropylidenediphenol (BPA):

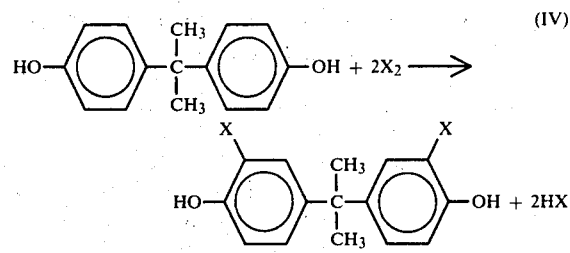

By minimizing the undesirable hydrogen halide co-product, HX, the formation of deleterious by-products and the absence of the characteristic, strong odor for chlorophenols are also minimized as illustrated by the following general equation:

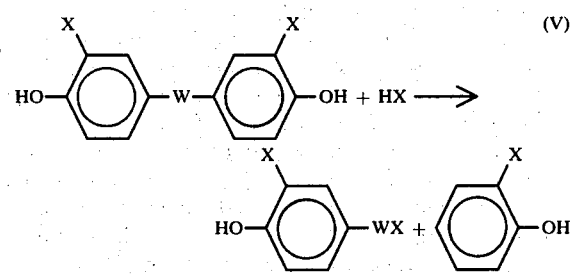

Accordingly, the halogenated diphenols produced using the process of this invention, which are readily recognizable by the formation of essentially colorless solutions, can be represented by the following general formula:

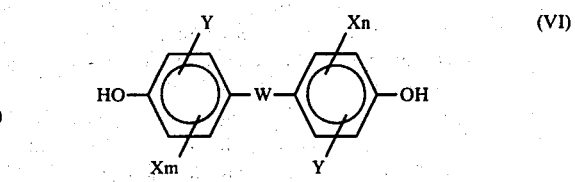

wherein Xm and Xn are each independently a halogen and mixtures thereof; Y is independently selected from the group consisting of $C_1$–$C_4$ alkyl and hydrogen; m and n are each 0–2 with the proviso that m+n equal at least 0.1, but no more than about 2.5; and, W is a member selected from the following group:

(a) —$CH_2$—$_r$ wherein r is 0–10 with the proviso that when both Xm and Xn are chlorine and m and n are each 1, r is 0 or 2–10;

(b)

wherein R is a member of the group consisting of $C_1$–$C_{10}$ alkyl and $C_6$–$C_{14}$ aryl;

(c)

wherein R and R' can each independently be the same as R in (b) above;

(d)

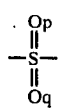

wherein p and q can each independently be 0–1; and, (e) —O—.

W and X are the same in the formulas for equations IV and V as described for formula VI.

In producing the diphenol of formula VI wherein W can be (a), (b) or (c), particularly (c), the formation of deleterious by-products is especially pronounced when employing prior art processes. When the process of this invention is employed, however, the formation of such deleterious by-products is dramatically minimized and virtually eliminated. Thus, the halogenated diphenols produced in accordance with this invention are virtually colorless or white as compared to the discolored halogenated diphenols obtained by prior art processes.

The temperature of the halogenation reaction can be about 0°–80° C., but is preferably held at about ambient temperature; i.e., 20°–35° C.

The amount of halogen added can vary depending upon the extent of halogenation desired. Thus, halogen can be added in amounts of about 0.1–2 moles per mole of diphenol employed.

Since the reaction in the process of the invention is based upon quantitative consumption of halogen, the process enables the degree of halogenation of the diphenol to be closely controlled. Accordingly, predetermined statistical mixtures of unreacted diphenol and reacted diphenol can be readily obtained. The amount of each obtained depends upon the moles of halogen added.

This is illustrated by the accompanying FIGURE.

As can be seen from the above FIGURE, a statistical maximum of 50 mole percent of monohalodiphenol obtains at a mole ratio of halogen:diphenol of 1:1, whereas a statistical maximum of essentially 100 mole percent dihalodiphenol obtains at a mole ratio of halogen:diphenol of 2:1. Accordingly, it is possible to produce essentially 100% of pure dihalodiphenol. Alternatively, statistical ternary mixtures comprising unreacted diphenol, monohalodiphenol and dihalodiphenol can be obtained as shown by the above diagram. This also pertains when mixtures of halogens are employed.

Typical of some of the diphenols that can be employed in this invention are bisphenol-A (2,2-bis(4-hydroxyphenyl)propane, also referred to as 4,4'-isopropylidenediphenol), bis(4-hydroxyphenyl)methane, 2,2-bis(4-hydroxy-3-methylphenyl)propane, 4,4-bis(4-hydroxyphenyl)heptane, 1,1-bis(4-hydroxyphenyl)ethane, 3-methyl-2,2-bis(4-hydroxyphenyl)propane, bis-(4-hydroxyphenyl)sulfone, bis-(4-hydroxyphenyl)ether, and the like. Other non-halogenated diphenols of the bisphenol type can also be used such as are disclosed in U.S. Pat. Nos. 2,999,835, 3,028,365 and 3,334,154.

PREFERRED EMBODIMENT OF THE INVENTION

The following examples are set forth to more fully and clearly illustrate the present invention and are intended to be, and should be construed as being, exemplary and not limitative of the invention. Unless otherwise stated, all parts and percentages are by weight.

EXAMPLE 1

Into a slurry of 228 g (1.0 mole) of 4,4'-isopropylidenediphenol (BPA) in 2L of methylene chloride, that was being purged by a slow stream of nitrogen, was introduced slowly at ambient temperature, in the course of about 2 hours, 142 g (2.0 moles) of chlorine gas. In the ensuing mildly exothermic reaction, the refluxing methylene chloride kept the reaction temperature between 40° and 45° C. After the addition of chlorine was completed, the colorless solution was sampled for gas chromatographic analysis, (6'×18" stainless steel, 5% Silicon OV-101 on Anakrom ABS (arylonitrile-butadiene-styrene) column, 80°–330° range, programmed at 8° C./minute). This showed the following composition:

| Compound | Retention Time (min.) | Composition (mole %) |
|---|---|---|
| 4,4'-isopropylidenediphenol | 17.2 | 0.3 |
| 2-chloro-4,4'-isopropylidenediphenol | 18.5 | 9.2 |
| 2,2'-dichloro-4,4'-isopropylidenediphenol | 19.9 | 89.7 |
| 2,2',6-trichloro-4,4'-isopropylidenediphenol | 21.0 | 0.7 |
| Reference (p-cumylphenol) | 13.1 | |

An additional 4.6 g (0.064 mole) of chlorine was added, still under nitrogen purge, and the solution analyzed. The BPA content was 0.0%; monochloro-BPA was 0.2%; dichloro-BPA was 98.4% and trichloro-BPA was 1.3%. Water (1 liter) was added to the reaction flask and stirred. Soon the reaction mixture became a white crystalline mass. After an hour, the crystals were filtered on sintered glass funnel, rinsed twice with water and air dried. The white crystals weighed 351 g, thus amounting to an essentially quantitative yield of 2,2'-dichloro-BPA trihydrate. The crystals melted at 90°–91° C. and had a 97.8% assay in dichloro-BPA content.

EXAMPLE 2

The procedure of Example 1 was repeated, except that the chlorination was carried out without a purge by an inert gas. A gradually deepening pink color soon developed that became cherry red at the end of the reaction. Workup, as described in Example 1, yielded pink crystals that, even after several recrystallizations, smelled of chlorophenols. The latter were identified also by gas chromatography, displaying a retention time of 4.2 min., whereas phenol emerged at 2.1 minutes and p-cumylphenol at 14.4 minutes.

EXAMPLE 3

The procedure of Example 1 was repeated, except that only one mole (71.0 g) of chlorine gas and carbon dioxide, as the inert purging gas, were used. At the end of the addition of chlorine, gas chromatography indicated the following composition:

| | Composition (mole %) |
|---|---|
| 4,4'-isopropylidenediphenol | 31.8 |
| 2-chloro-4,4'-isopropylidenediphenol | 48.1 |
| 2,2'-dichloro-4,4'-isopropylidenediphenol | 20.1 |
| 2,2',6-trichloro-4,4'-isopropylidenediphenol | 0.0 |

-continued

| | Composition (mole %) |
|---|---|
| By adding an additional 7.0 g (0.1 mole) of chlorine, a truly statistical mixture resulted. | |
| 4,4'-isopropylidenediphenol | 25.8 |
| 2-chloro-4,4'-isopropylidenedephenol | 51.0 |
| 2,2'-dichloro-4,4'-isopropylidenediphenol | 23.0 |
| 2,2',6-trichloro-4,4'-isopropylidenediphenol | 0.2 |

EXAMPLE 4

The procedure of Example 2 was repeated, except that an equivalent amount of 4,4'-(2,2,2-trichloroethylidene)diphenol and neon gas were substituted for 4,4'-isopropylidenediphenol and carbon dioxide, respectively. Gas chromatography showed the following composition at the end of the reaction.

| Compound | Retention Time (min.) | Composition (mole %) |
|---|---|---|
| 4,4'-(2,2,2-trichloroethylidene)diphenol | 20.18 | 28.7 |
| 2-chloro-4,4'-(2,2,2-trichloroethylidene)diphenol | 21.30 | 47.6 |
| 2,2'-dichloro-4,4'-(2,2,2-trichloroethylidene)diphenol | 22.20 | 23.6 |
| 2,2',6-trichloro-4,4'-(2,2,2-trichloroethylidene)diphenol | 23.02 | 0.1 |
| Reference (p-cumylphenol) | 12.67 | |

EXAMPLE 5

The procedure of Example 1 was repeated, except that an equivalent amount of 4,4'-(dichlorovinylidene)diphenol and methyl chloride gas were substituted for BPA and nitrogen, respectively. Also, the reaction was carried out in darkness. At the end of the reaction, the following composition was indicated by gas chromatography:

| Compound | Retention Time (min.) | Composition (mole %) |
|---|---|---|
| 4,4'-(dichlorovinylidene)diphenol | 18.97 | 0.2 |
| 2-chloro-4,4'-(dichlorovinylidene)diphenol | 20.11 | 8.6 |
| 2,2'-dichloro-4,4'-(dichlorovinylidene)diphenol | 20.91 | 91.0 |
| 2,2',6'-trichloro-4,4'-(dichlorovinylidene)diphenol | 21.91 | 0.2 |
| Reference (p-cumylphenol) | 12.36 | |

Recrystallization from hexane yielded white crystals of 2,2'-dichloro-4,4'-(dichlorovinylidene)diphenol with an assay of 98.0% and mp of 109°–110.5° C.

EXAMPLE 6

The procedure of Example 1 was repeated, except that 4,4'-(cyclohexylidene)diphenol (BPC) was substituted in equivalent amounts for BPA. The following composition was indicated at the end of the reaction by gas chromatography:

| Compound | Retention Time (min.) | Composition (mole %) |
|---|---|---|
| 4,4'-(cyclohexylidene)diphenol | 19.57 | 0.1 |
| 2-chloro-4,4'-(cyclohexylidene)diphenol | 20.82 | 5.6 |
| 2,2'-dichloro-4,4'-(cyclohexylidene)diphenol | 23.15 | 92.1 |
| 2,2',6-trichloro-4,4'-(cyclohexylidene)diphenol | | 2.2 |
| Reference (4-cumylphenol) | 12.36 | |

Recrystallization from water-methanol yielded colorless crystals, 99.6% pure, melting point 148.5°–149.5° C.

EXAMPLE 7

The procedure of Example 1 was repeated, except that an equivalent amount of 4,4'-cyclohexylidenedi-o-cresol and sulfur dioxide gas were substituted for BPA and nitrogen, respectively. Gas chromatography indicated the following composition at the end of the reaction:

| Compound | Retention Time (min.) | Composition (mole %) |
|---|---|---|
| 4,4'-cyclohexylidenedi-o-cresol | 22.72 | 0.6 |
| 2-chloro-4,4'-cyclohexylidenedi-o-cresol | 24.01 | 3.9 |
| 2,2'-dichloro-4,4'-cyclohexylidenedi-o-cresol | 25.44 | 95.4 |
| 2,2',6-trichloro-4,4'-cyclohexylidenedi-o-cresol | 26.96 | 0.1 |
| Reference (p-cumylphenol) | 14.93 | |

Recrystallization from methanol-water yielded 2,2'-dichloro-4,4'-cyclohexylidenedi-o-cresol in 98.8% purity and with a 136.5°–137.5° C. melting point.

EXAMPLE 8

The procedure of Example 1 was repeated, except that an equivalent amount of 4,4'-sulfonyldiphenol was substituted for BPA. Filtration of unreacted starting material and gas chromatographic analysis of the filtrate indicated the following composition:

| Compound | Retention Time (min.) | Composition (mole %) |
|---|---|---|
| 4,4'-sulfonyldiphenol | 23.37 | 10.2 |
| 2-chloro-4,4'-sulfonyldiphenol | 24.22 | 31.3 |
| 2,2'-dichloro-4,4'-sulfonyldiphenol | 25.05 | 58.3 |
| 2,2',6-trichloro-4,4'-sulfonyldiphenol | 75.86 | 0.2 |
| Reference (p-cumylphenol) | 15.73 | |

EXAMPLE 9

The procedure of Example 1 was repeated, except that the halogen added was 0.5 moles of bromine followed by 1.5 moles of chlorine. Gas chromatography of the final product indicated the following composition.

| Compound | Retention Time (min.) | Composition (mole %) |
|---|---|---|
| 4,4'-isopropylidenephenol | 17.10 | 0.1 |
| 2-chloro-4,4'-isopropylidenediphenol | 18.31 | 6.7 |
| 2-bromo-4,4'-isopropylidenediphenol | 18.90 | 2.2 |
| 2,2'-dichloro-4,4'-isopropylidenediphenol | 19.81 | 50.2 |
| 2-bromo-2'-chloro-4,4'-isopropylidenediphenol | 20.67 | 32.9 |
| 2,2'-dibromo-4,4'-isopropylidenediphenol | 21.11 | 7.2 |
| 2-bromo-2',6-dichloroisopropylidene- | 21.57 | 0.3 |

| Compound | Retention Time (min.) | Composition (mole %) |
|---|---|---|
| diphenol | | |
| 2-chloro-2',6'-dibromoisopropylidene-diphenol | 21.98 | 0.2 |
| 2,2',6-tribromoisopropylidenediphenol | 22.79 | 0.0 |
| 2,2',6-trichloroisopropylidenediphenol | 20.82 | 0.2 |
| Reference (p-cumylphenol) | 13.02 | |

As mentioned earlier, the process disclosed in German Pat. No. P25 317.2 results in producing a mixture of unreacted bisphenol and statistical mixtures of halogenated bisphenol whereas the process of this invention, as shown by the foregoing examples, results in producing true statistical mixtures comprising unreacted bisphenol, monohalobisphenol and dihalobisphenols.

What is claimed is:

1. A halogenated diphenol mixture having a significantly reduced quantity of trihalo substituted and tetrahalo substituted diphenol, said mixture containing predetermined, statistical quantities of unreacted diphenol, monohalodiphenol and dihalodiphenol, said halogenated diphenol being represented by the general formula:

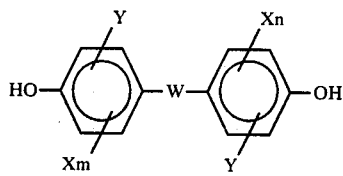

wherein Xm and Xn are each independently a halogen and mixtures thereof; Y is independently selected from the group consisting of $C_1$–$C_4$ alkyl and hydrogen; m and n are each 0–2 with the proviso that m+n equal at least 0.1, but more than 2.0; and, W is a member selected from the following group:

(a) —$CH_2$—$_r$ wherein r is 0–10 with the proviso that when both Xm and Xn are chlorine and m and n are each 1, r is 0 or 2–10;

(b)

wherein R is a member of the group consisting of $C_1$–$C_{10}$ alkyl and $C_6$–$C_{14}$ aryl;

(c)

wherein R and R' can each independently be the same as R in (b) above;

(d)

wherein p and q can each independently be 0–1; and, (e) —O— (e) cyclohexylidene; (f) 2,2,2-trichloroethylidene; (h) dichlorovinylidene.

2. The halogenated diphenol of claim 1 wherein said diphenol is 2,2-bis(4-hydroxyphenyl)propane.

3. The halogenated diphenol of claim 2 wherein W is (b).

4. The halogenated diphenol of claim 2 wherein W is (c).

5. The halogenated diphenol of claim 1 wherein Xm and Xn are each bromine and m+n equal 2.0.

6. The halogenated diphenol of claim 1 wherein Xm and Xn are each chlorine and m+n equal 2.0.

7. The halogenated diphenol of claim 1 wherein Xm is chlorine, Xn is bromine and m+n equal 2.0.

8. The halogenated diphenol of claim 5 wherein Y is hydrogen.

9. The halogenated diphenol of claim 5 wherein Y is $CH_3$.

10. The halogenated diphenol of claim 6 wherein Y is hydrogen.

11. The halogenated diphenol of claim 6 wherein Y is $CH_3$.

12. The halogenated diphenol of claim 7 wherein Y is hydrogen.

13. The halogenated diphenol of claim 7 wherein Y is $CH_3$.

* * * * *

UNITED STATES PATENT AND TRADEMARK OFFICE
CERTIFICATE OF CORRECTION

PATENT NO. : 4,291,177
DATED : September 22, 1981
INVENTOR(S) : Victor Mark and Charles Adelbert Wilson, II It is certified that error appears in the above-identified patent and that said Letters Patent are hereby corrected as shown below:

Column 9, line 15

"German Pat. No. P25 317.2" - should be -

"German Pat. No. P25 20 317.2"

Signed and Sealed this

Seventh Day of June 1983

[SEAL]

Attest:

DONALD J. QUIGG

Attesting Officer     Acting Commissioner of Patents and Trademarks